US009988365B2

(12) United States Patent
Hoekstra et al.

(10) Patent No.: US 9,988,365 B2
(45) Date of Patent: Jun. 5, 2018

(54) 2-(2,4-DIFLUOROPHENYL)-1,1-DIFLUORO-1-(5-SUBSTITUTED-PYRIDIN-2-YL)-3-(1H-TETRAZOL-1-YL)PROPAN-2-OLS AND PROCESSES FOR THEIR PREPARATION

(71) Applicant: Viamet Pharmaceuticals, Inc., Durham, NC (US)

(72) Inventors: William J. Hoekstra, Durham, NC (US); Nakyen Choy, Carmel, IN (US); Carl DeAmicis, Indianapolis, IN (US); Daniel Knueppel, Zionsville, IN (US); Jim Renga, Indianapolis, IN (US); Michael T. Sullenberger, Westfield, IN (US); Gregory Whiteker, Carmel, IN (US); Yuanming Zhu, Carmel, IN (US); Gary D. Gustafson, Zionsville, IN (US)

(73) Assignee: VPS-3, Inc., Durham, NC (US)

( * ) Notice: Subject to any disclaimer, the term of this patent is extended or adjusted under 35 U.S.C. 154(b) by 0 days. days.

(21) Appl. No.: 15/126,353

(22) PCT Filed: Mar. 19, 2015

(86) PCT No.: PCT/US2015/021527
§ 371 (c)(1),
(2) Date: Sep. 15, 2016

(87) PCT Pub. No.: WO2015/143192
PCT Pub. Date: Sep. 24, 2015

(65) Prior Publication Data
US 2017/0158667 A1    Jun. 8, 2017

Related U.S. Application Data

(60) Provisional application No. 61/955,680, filed on Mar. 19, 2014.

(51) Int. Cl.
| C07D 403/06 | (2006.01) |
| C07D 401/06 | (2006.01) |
| C07D 257/04 | (2006.01) |
| C07D 401/14 | (2006.01) |
| C07D 213/65 | (2006.01) |
| C07D 401/12 | (2006.01) |
| C07D 213/50 | (2006.01) |

(52) U.S. Cl.
CPC ......... C07D 401/14 (2013.01); C07D 213/50 (2013.01); C07D 213/65 (2013.01); C07D 401/06 (2013.01); C07D 401/12 (2013.01)

(58) Field of Classification Search
CPC .. C07D 401/14; C07D 213/50; C07D 213/65; C07D 401/06; C07D 401/12
USPC ...................................................... 546/256
See application file for complete search history.

(56) References Cited

U.S. PATENT DOCUMENTS

| 4,426,531 | A | 1/1984 | Bison et al. |
| 8,236,962 | B2 | 8/2012 | Hoekstra et al. |
| 8,748,461 | B2 | 6/2014 | Hoekstra et al. |
| 8,754,227 | B2 | 6/2014 | Hoekstra et al. |
| 8,796,001 | B2 | 8/2014 | Hoekstra et al. |
| 8,809,378 | B2 | 8/2014 | Hoekstra et al. |
| 8,883,785 | B2 | 11/2014 | Dominguez |
| 8,883,797 | B2 | 11/2014 | Hoekstra et al. |
| 8,901,121 | B2 | 12/2014 | Hoekstra et al. |
| 8,940,735 | B2 | 1/2015 | Hoekstra et al. |
| 9,220,265 | B2 | 12/2015 | Hoekstra et al. |
| 9,221,791 | B2 | 12/2015 | Hoekstra et al. |
| 9,309,273 | B2 | 4/2016 | Hoekstra et al. |
| 9,414,596 | B2 | 8/2016 | Hoekstra et al. |
| 9,447,073 | B2 | 9/2016 | Hoekstra et al. |
| 9,556,143 | B2 | 1/2017 | Hoekstra et al. |
| 9,663,488 | B2 | 5/2017 | Hoekstra et al. |
| 9,688,671 | B2 | 6/2017 | Hoekstra et al. |
| 2009/0318436 | A1* | 12/2009 | Albrecht ............... C07D 471/04 514/233.2 |
| 2011/0306644 | A1* | 12/2011 | Hoekstra ............... C07D 401/06 514/341 |
| 2012/0329788 | A1 | 12/2012 | Hoekstra et al. |
| 2012/0329802 | A1 | 12/2012 | Hoekstra et al. |
| 2013/0005719 | A1 | 1/2013 | Hoekstra et al. |
| 2013/0005729 | A1 | 1/2013 | Hoekstra et al. |
| 2013/0005752 | A1 | 1/2013 | Hoekstra et al. |
| 2013/0005776 | A1 | 1/2013 | Hoekstra et al. |
| 2013/0012503 | A1 | 1/2013 | Hoekstra et al. |
| 2014/0288107 | A1 | 9/2014 | Hoekstra et al. |
| 2014/0350003 | A1 | 11/2014 | Hoekstra et al. |
| 2015/0004666 | A1 | 1/2015 | Hoekstra et al. |
| 2015/0024938 | A1 | 1/2015 | Hoekstra et al. |
| 2015/0099750 | A1 | 4/2015 | Hoekstra et al. |

(Continued)

FOREIGN PATENT DOCUMENTS

| CN | 1126722 A | 7/1996 |
| CN | 1334811 A | 2/2002 |

(Continued)

OTHER PUBLICATIONS

Biju; Synthetic Communications, 2008, 38, 1940-1945.*
Eto; Chemical and Pharmaceutical Bulletin, 2000, 48, 982-990.*
Shimizu; Tetrahedron Letters, 1997, 38, 2685-2688.*
International Search Report and Written Opinion dated Jun. 25, 2015 for Application No. PCT/US2015/021436.
International Search Report and Written Opinion dated Jun. 29, 2015 for Application No. PCT/US2015/021445.
International Search Report and Written Opinion dated Jun. 26, 2015 for Application No. PCT/US2015/021519.

(Continued)

Primary Examiner — Daniel R Carcanague
(74) Attorney, Agent, or Firm — Wolf, Greenfield & Sacks, P.C.

(57) ABSTRACT

Provided herein are 2-(2,4-difluorophenyl)-1,1-difluoro-1-(5-substituted-pyridin-2-yl)-3-(1H-tetrazol-1-yl)propan-2-ols and 1-(2,4-difluorophenyl)-2,2-difluoro-2-(5-substituted-pyridin-2-yl)ethanones and processes for their preparation.

21 Claims, No Drawings

(56) References Cited

U.S. PATENT DOCUMENTS

| | | | |
|---|---|---|---|
| 2016/0214959 | A1 | 7/2016 | Hoekstra et al. |
| 2017/0081285 | A1 | 3/2017 | Hoekstra et al. |
| 2017/0081309 | A1 | 3/2017 | Hoekstra et al. |
| 2017/0081310 | A1 | 3/2017 | Hoekstra et al. |
| 2017/0081316 | A1 | 3/2017 | Hoekstra et al. |
| 2017/0088539 | A1 | 3/2017 | Hoekstra et al. |
| 2017/0088540 | A1 | 3/2017 | Hoekstra et al. |
| 2017/0096410 | A1 | 4/2017 | Hoekstra et al. |
| 2017/0121307 | A1* | 5/2017 | Hoekstra .............. C07D 401/06 |
| 2017/0144990 | A1* | 5/2017 | Hoekstra .............. C07D 213/56 |
| 2017/0144991 | A1* | 5/2017 | Hoekstra .............. C07D 213/38 |

FOREIGN PATENT DOCUMENTS

| | | | |
|---|---|---|---|
| CN | 102811620 A | | 12/2012 |
| JP | 2000-344744 A | | 12/2000 |
| WO | WO 00/37459 A1 | | 6/2000 |
| WO | WO 2014-193974 A1 | | 12/2004 |
| WO | WO 2009/020323 A2 | | 2/2009 |
| WO | WO 2010/146113 A1 | | 12/2010 |
| WO | WO 2010/147302 A2 | | 12/2010 |
| WO | WO 2011/133875 A2 | | 10/2011 |
| WO | WO 2012/177608 A1 | | 12/2012 |
| WO | WO 2012/177635 A1 | | 12/2012 |
| WO | WO 2012/177725 A1 | | 12/2012 |
| WO | WO 2012/177728 A1 | | 12/2012 |
| WO | WO2012177603 | * | 12/2012 |
| WO | WO 2013/109998 A1 | | 7/2013 |
| WO | WO 2013/110002 A1 | | 7/2013 |
| WO | WO2014043376 | * | 3/2014 |
| WO | WO2014165861 | * | 10/2014 |
| WO | WO 2015/143184 A1 | | 9/2015 |
| WO | WO 2015/143192 A1 | | 9/2015 |
| WO | WO2015143154 | * | 9/2015 |
| WO | WO2015143162 | * | 9/2015 |
| WO | WO2016187201 | * | 11/2016 |
| WO | WO2017049080 | * | 3/2017 |
| WO | WO2017049096 | * | 3/2017 |
| WO | WO2017049196 | * | 3/2017 |
| WO | WO 2017/087592 A1 | | 5/2017 |
| WO | WO 2017/087597 A1 | | 5/2017 |
| WO | WO 2017/087619 A1 | | 5/2017 |
| WO | WO 2017/087643 A1 | | 5/2017 |
| WO | WO 2017/117393 A1 | | 7/2017 |

OTHER PUBLICATIONS

International Search Report and Written Opinion dated Jun. 29, 2015 for Application No. PCT/US2015/021527.
International Search Report and Written Opinion dated Jul. 14, 2015 for Application No. PCT/US2015/021464.
International Search Report and Written Opinion dated Jul. 14, 2015 for Application No. PCT/US2015/021476.
International Search Report and Written Opinion dated Jul. 10, 2015 for Application No. PCT/US2015/021484.
International Search Report and Written Opinion dated Jun. 24, 2015 for Application No. PCT/US2015/021491.
International Search Report and Written Opinion dated Jun. 26, 2015 for Application No. PCT/US2015/021504.
International Search Report and Written Opinion dated Jun. 24, 2015 for Application No. PCT/US2015/021511.
Partial Supplementary European Search Report and Search Opinion dated Jul. 13, 2017 for EP Application No. 15765715.6.
Partial Supplementary European Search Report and Search Opinion dated Aug. 3, 2017 for EP Application No. 15764600.1.
Extended European Search Report and Search Opinion dated Aug. 1, 2017 for EP Application No. 15764570.6.
Extended European Search Report and Search Opinion dated Aug. 23, 2017 for EP Application No. 15765402.1.
Partial Supplementary European Search Report and Search Opinion dated Jul. 19, 2017 for EP Application No. 15764259.6.
Extended European Search Report and Search Opinion dated Jul. 3, 2017 for EP Application No. 15764654.8.
Extended European Search Report and Search Opinion dated Aug. 1, 2017 for EP Application No. 15764368.5.
Extended European Search Report and Search Opinion dated Jul. 21, 2017 for EP Application No. 15764743.9.
Extended European Search Report and Search Opinion dated Jul. 21, 2017 for EP Application No. 15764771.0.
Extended European Search Report and Search Opinion dated Jul. 13, 2017 for EP Application No. 15765307.2.
International Search Report and Written Opinion dated Feb. 3, 2017 for Application No. PCT/U52016/032877.
Kolb et al., Catalytic Asymmetric Dihydroxylation. Chemical Reviews 1994;94(8):2483-2547. doi: 10.1021/cr00032a009.
Uemura et al., Enantioselective Cyanosilylation of Ketones with Amino Acid/BINAP/Ruthenium(II)-Lithium Phenoxide Catalyst System. Advanced Synthesis & Catalysis. Jul. 2012;354(10):2023-30. doi: 10.1002/adsc.201200027.
Clemencon et al., Tandem Multicomponent/Click Reactions: Synthesis of Functionalized Oxazoles and Tetrazoles from Acyl Cyanides. Tetrahedron. 2007;63:8665-9.
Demko et al., A Click Chemistry Approach to Tetrazoles by Huisgen 1,3-Dipolar Cycloaddition: Synthesis of 5-Sulfonyl Tetrazoles from Azides and Sulfonyl Cyanides. Angew. Chem. Int. Ed. Dec. 2002;41(12):2110-3.
Otsuki et al., Chemical tagging of a drug target using 5-sulfonyl tetrazole. Bioorg Med Chem Lett. Mar. 15, 2013;23(6):1608-11. doi:10.1016/j.bmcl.2013.01.092. Epub Jan. 30, 2013.
Putis et al. Tetrazole-containing derivatives of 4-amino-3-phenylbutanoic acid. Arkivoc. Dec. 2009; 2009(4): 64-8. doi: http://dx.doi.org/10.3998/ark.5550190.0010.406.

* cited by examiner

2-(2,4-DIFLUOROPHENYL)-1,1-DIFLUORO-1-(5-SUBSTITUTED-PYRIDIN-2-YL)-3-(1H-TETRAZOL-1-YL)PROPAN-2-OLS AND PROCESSES FOR THEIR PREPARATION

CROSS REFERENCE TO RELATED APPLICATIONS

This application is the U.S. National Stage, pursuant to 35 U.S.C. § 371, of International Application No. PCT/US2015/021527, filed Mar. 19, 2015, which claims the benefit of U.S. Provisional Patent Application Ser. No. 61/955,680 filed Mar. 19, 2014, the entire disclosures of which are incorporated by reference herein.

FIELD

Provided herein are 2-(2,4-difluorophenyl)-1,1-difluoro-1-(5-substituted-pyridin-2-yl)-3-(1H-tetrazol-1-yl)propan-2-ols and processes for their preparation. In another embodiment provided herein are 1-(2,4-difluorophenyl)-2,2-difluoro-2-(5-substituted-pyridin-2-yl)ethanones and processes for their preparation.

BACKGROUND

U.S. patent application Ser. Nos. 13/527,387, 13/527,426 and 13/528,283 describe inter alia certain metalloenzyme inhibitor compounds and their use as fungicides. The disclosure of each application is expressly incorporated by reference herein. Each of these patents describes the various routes to generate metalloenzyme inhibiting fungicides. It may be advantageous to provide more direct and efficient methods for the preparation of metalloenzyme inhibiting fungicides and related compounds, e.g., by the use of reagents and/or chemical intermediates which provide improved time and cost efficiency.

SUMMARY OF THE DISCLOSURE

Provided herein are 2-(2,4-difluorophenyl)-1,1-difluoro-1-(5-substituted-pyridin-2-yl)-3-(1H-tetrazol-1-yl)propan-2-ols and 1-(2,4-difluorophenyl)-2,2-difluoro-2-(5-substituted-pyridin-2-yl)ethanones and processes for their preparation. In one embodiment, provided herein is a process for the preparation of a compound of the Formula VI:

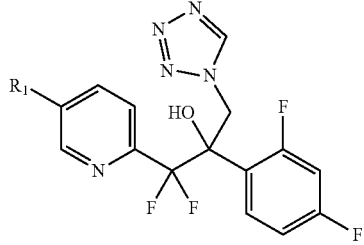
(VI)

wherein $R_1$ is selected from:

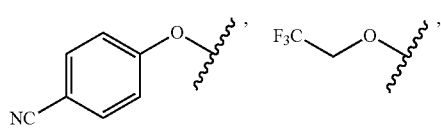

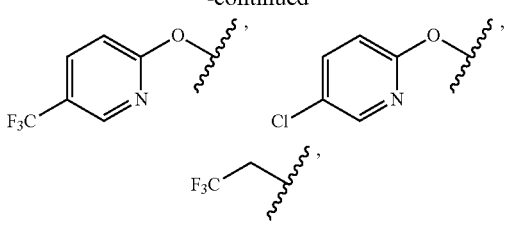

and Br,
which comprises contacting compounds of Formula V with triethyl orthoformate and sodium azide in the presence of acetic acid.

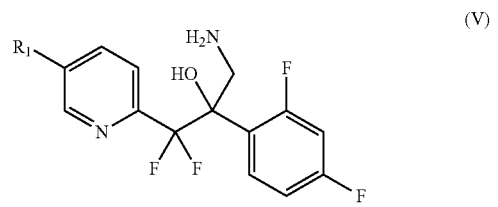
(V)

In another embodiment, compounds of Formula V may be prepared by contacting compounds of Formula IV with a metal and an acid selected from acetic acid and hydrochloric acid.

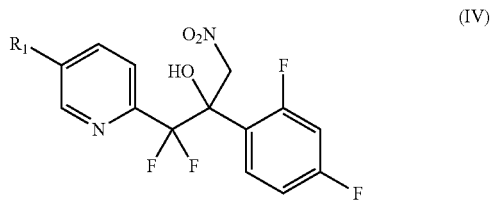
(IV)

In another embodiment, compounds of Formula IV may be prepared by contacting compounds of Formula III with nitromethane and a base.

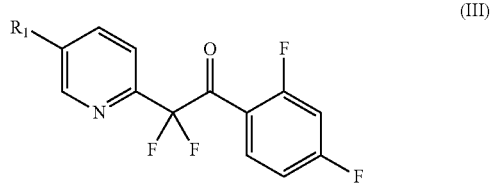
(III)

In another embodiment, compounds of Formula III may be prepared by contacting compounds of Formula II with a preformed organometallic reagent.

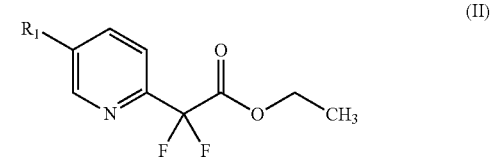
(II)

In another embodiment, compounds of Formula III may be prepared by contacting compounds of Formula IIa with a preformed organometallic reagent.

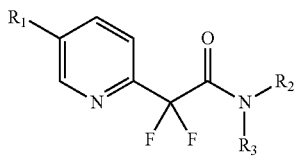

(IIa)

In another embodiment, compounds of Formula IIa may be prepared by contacting compounds of Formula II with an amine, a Lewis acid, and a solvent.

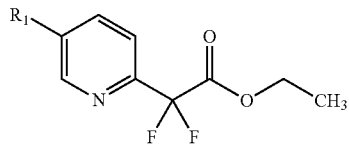

(II)

In another embodiment, compounds of Formula II may be prepared by contacting compounds of the Formula I with ethyl 2-bromo-2,2-difluoroacetate and a metal.

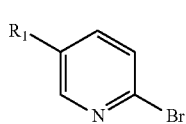

(I)

The term "cyano" refers to a —C≡N substituent.
The term "hydroxyl" refers to an —OH substituent.
The term "amino" refers to a —NH$_2$ substituent.
The term "alkylamino" refers to a —N(H)—R substituent.
The term "dialkylamino" refers to a —NR$_2$ substituent.
The term "halogen" or "halo" refers to one or more halogen atoms, defined as F, Cl, Br, and I.
The term "nitro" refers to a —NO$_2$ substituent.
The term "Lewis acid" refers to any substance that is an electron pair acceptor.
The term "organometallic" refers to an organic compound containing a metal, especially a compound in which a metal atom is bonded directly to a carbon atom.

Throughout the disclosure, references to the compounds of Formula VII, VI, V, and IV are read as also including optical isomers and salts. Specifically, when compounds of Formula VII, VI, V, or IV contain a branched chain alkyl group, it is understood that such compounds include optical isomers and racemates thereof. Exemplary salts may include: hydrochloride, hydrobromide, hydroiodide, and the like. Additionally, the compounds of Formula VII, VI, V, and IV may include tautomeric forms.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

The embodiments described above are intended merely to be exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

DETAILED DESCRIPTION 2-(2,4-Difluorophenyl)-1,1-difluoro-1-(5-substituted-pyridin-2-yl)-3-(1H-tetrazol-1-yl)propan-2-ols and 1-(2,4-difluorophenyl)-2,2-difluoro-2-(5-substituted-pyridin-2-yl) ethanones provided herein may be prepared from 6-bromopyridin-3-ol as shown in Examples 1-8.

Example 1: Preparation of 4-((6-bromopyridin-3-yl)oxy)benzonitrile (1)

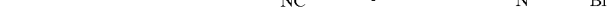

Method A:
To a stirred solution of 6-bromopyridin-3-ol (5.0 g, 28.7 mmol) and 4-fluorobenzonitrile (3.48 g, 28.7 mmol) in dry DMSO (57.5 mL) under nitrogen was added cesium carbonate (14.04 g, 43.1 mmol). The reaction mixture was stirred at 75° C. for 18 h. The reaction was poured into ice water. The pH was adjusted to make the solution mildly acidic (pH=6) using 1 N HCl. The resulting precipitate was filtered and washed with water followed by a minimum amount of ether to give the title compound as a brown solid (6.292 g, 76%).

Method B:
To a stirred solution of 6-bromopyridin-3-ol (17.3 g, 100 mmol) and 4-fluorobenzonitrile (12.1 g, 120 mmol) in DMF (150 mL) under nitrogen was added Cs$_2$CO$_3$ (32.5 g, 120 mmol). The reaction mixture was stirred at 85-90° C. for 10-15 h. HPLC indicated the reaction was complete. Into the reaction mixture cooled to 10-15° C. (ice bath) was charged water (450 mL) to precipitate the product. The resulting precipitate was filtered, washed with acetonitrile-water (1:4) and water, and dried in a vacuum oven to give the title compound as a white solid (25 g, 91%). The product was slurried in EtOH (50 mL) at room temperature for 2-3 h to remove the side product. The suspension was filtered to collect the title compound as a white solid (23.5 g, 85%).

This reaction was also carried out as described in Example 1, Method A with the exception that potassium carbonate was used in place of cesium carbonate.

The following compounds 1-3 in Table 1a were made in accordance with the reaction depicted in Scheme 1 and the procedures described in Example 1. Characterization data for compounds 1-3 are shown in Table 1b.

Scheme 1

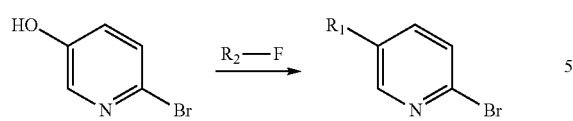

TABLE 1a

| Compound No. | R₁ | Appearance | Prepared as in Example(s): | R₂—F |
|---|---|---|---|---|
| 1 | 4-cyanophenoxy | Brown solid | Ex 1, Methods A and B | 4-fluorobenzonitrile |
| 2 | 5-(trifluoromethyl)pyridin-2-yloxy | Off-white solid | Ex 1, Method B | 2-fluoro-5-(trifluoromethyl)pyridine |
| 3 | 5-chloropyridin-2-yloxy | White Solid | Ex 1, Method B | 5-chloro-2-fluoropyridine |

TABLE 1b

| Compound No. | Mp (°C.) | ESIMS m/z | $^1$H NMR (δ)[a] | $^{13}$C NMR or $^{19}$F NMR (δ) | IR(thin film) cm$^{-1}$ |
|---|---|---|---|---|---|
| 1 | 113 | 275 ([M]⁺) | 8.22 (d, J = 2.9 Hz, 1H), 7.70-7.63 (m, 2H), 7.56-7.51 (m, 1H), 7.28 (dd, J = 8.5, 2.9 Hz, 1H), 7.10-7.02 (m, 2H) | | |
| 2 | | | 8.39-8.32 (m, 1H), 8.27-8.22 (m, 1H), 7.97-7.85 (m, 1H), 7.49 (dd, J = 8.6, 0.5 Hz, 1H), 7.41 (dd, J = 8.6, 2.9 Hz, 1H), 7.09 (d, J = 8.7 Hz, 1H) | $^{13}$C NMR (101 MHz, CDCl₃) δ 164.46 (s), 149.27 (s), 145.02 (q, J = 4.3 Hz), 143.88 (s), 139.03-134.92 (m), 132.18 (s), 128.54 (s), 124.81 (s), 122.54 (q, J = 33.3 Hz), 122.12 (s), 111.83 (s) | |
| 3 | | 284 ([M]⁺) | 8.27 (dd, J = 3.0, 0.6 Hz, 1H), 8.08 (dd, J = 2.7, 0.7 Hz, 1H), 7.71 (dd, J = 8.7, 2.6 Hz, 1H), 7.51 (dd, J = 8.6, 0.6 Hz, 1H), 7.41 (dd, J = 8.6, 2.9 Hz, 1H), 6.98 (dd, J = 8.7, 0.7 Hz, 1H) | | |

[a] All $^1$H NMR data measured in CDCl₃ at 400 MHz unless otherwise noted

Example 2. Preparation of 2-bromo-5-(2,2,2-trifluoroethoxy)pyridine

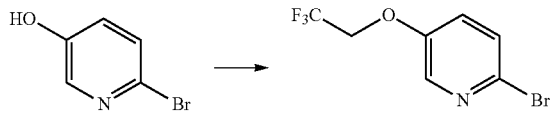 [SMILES: Oc1ccc(Br)nc1 ; FC(F)(F)COc1ccc(Br)nc1]

6-Bromopyridin-3-ol (32.5 g, 187 mmol) and cesium carbonate (70.6 g, 217 mmol) were placed into a 1 L, 3-neck Morton flask equipped with a temperature probe, an overhead stirrer, and an addition funnel topped with a nitrogen line. A 9° C. cooling bath was applied before the solids were charged with DMF (325 mL). The temperature increased from 15° C. to 20° C. when 2,2,2-trifluoroethyl trifluoromethanesulfonate (30.8 mL, 50.6 g, 212 mmol) was added by syringe over 27 min to the heterogeneous mixture of other components. The purple solution was stirred for 1 h 40 min before re-cooling with a 10° C. water bath. The solution was cooled to room temperature after the addition of water (650 mL). The mixture was extracted five times with 200 mL portions of 3:1 hexane-ethyl acetate. The combined organic layers were washed three times with 150 mL portions of water, dried over $Na_2SO_4$, filtered, and concentrated. The oil was then concentrated twice from 100 mL portions of hexane to give the title compound as a white solid (47.21 g, 99%): $^1$H NMR (400 MHz, $CDCl_3$) δ 8.12 (d, J=3.2 Hz, 1H), 7.44 (dd, J=8.8, 0.6 Hz, 1H), 7.19 (dd, J=8.7, 3.2 Hz, 1H), 4.40 (q, J=7.9 Hz, 2H); $^{19}$F NMR −73.87; ESIMS m/z 256 ($[M+H]^+$).

Example 3: Preparation of ethyl 2-(5-(4-cyanophenoxy)pyridin-2-yl)-2,2-difluoroacetate (5)

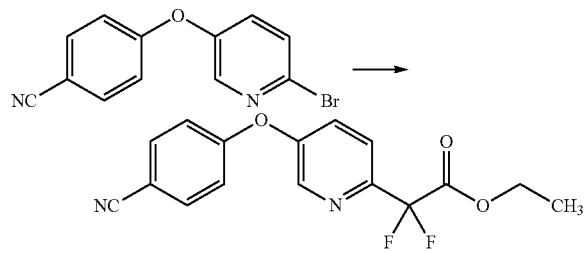

Method A:

Crude 4-((6-bromopyridin-3-yl)oxy)benzonitrile was dried azeotropically with toluene to remove any possible trace water from the starting material. A magnetically stirred mixture of ethyl 2-bromo-2,2-difluoroacetate (3.08 mL, 23.99 mmol) and copper (2.98 g, 46.9 mmol) in dry DMSO (33.7 mL) was stirred at rt for 1 h, then 4-((6-bromopyridin-3-yl)oxy)benzonitrile (5.57 g, 20.25 mmol) was added in one portion. The reaction mixture was stirred at 60° C. for 3 days. The reaction was determined to be complete by TLC. The heat source was removed and the reaction diluted with EtOAc (100 mL) and stirred for 20 minutes. The reaction was filtered through a plug of celite and washed with EtOAc. The filtrate was washed with saturated $NH_4Cl$ (3×) to remove any remaining copper. The solution was dried, and the solvent was removed under reduced pressure to produce crude product as a brown oil (5.947 g, 83%). The residue was purified by silica gel chromatography (0-20% EtOAc/hexanes) to give the title compound as a clear oil (two lots: (3.897 g, 59.9%, 99% purity) and (804 mg, 11.23%, 90% purity).

Method B:

A magnetically stirred mixture of 4-((6-bromopyridin-3-yl)oxy)benzonitrile (27.5 g, 20 mmol), ethyl 2-bromo-2,2-difluoroacetate (4.47 g, 22 mmol), copper (2.67 g, 42 mmol) and methanesulfonic acid (38 mg, 0.4 mmol) in dry DMF (50 mL) was stirred at 40-45° C. The reaction was complete by HPLC. The reaction mixture was cooled to room temperature, then diluted with toluene (200 mL) and stirred for 0.5 h at room temperature before filtration through celite and washing with additional toluene. The filtrate was washed with 20% $NH_4Cl$ (50 mL) and water (25 mL×2). The organic layer was concentrated with additional acetonitrile under reduced pressure to remove water. The solution was concentrated and dried under in vacuo to give the title compound as a brown oil (5.3 g, 83%).

The following compounds 5-10 in Table 3a were made in accordance with the reaction depicted in Scheme 3 and the procedures described in Example 3. Characterization data for compounds 5-10 are shown in Table 3b.

Scheme 3

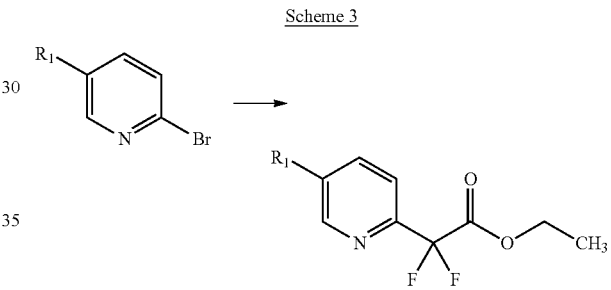

TABLE 3a

| Compound No. | $R_1$ | Appearance | Prepared as in Example(s): |
|---|---|---|---|
| 5 | | Brown oil | Ex 3, Methods A and B |
| 6 | $F_3C$-CH_2-O- | Amber oil | Ex 3, Method B |
| 7 | $F_3C$-pyridyl-O- | Colorless oil | Ex 3, Method B |
| 8 | Cl-pyridyl-O- | Brown oil | Ex 3, Method B |
| 9 | Br | Clear Colorless oil | Ex 3, Method A |

TABLE 3a-continued

| Compound No. | R₁ | Appearance | Prepared as in Example(s): | |
|---|---|---|---|---|
| 10 | F₃C-(structure) | Yellow oil | Ex 3, Method B | 5 |

TABLE 3b

| Compound No. | Mp (° C.) | ESIMS m/z | ¹H NMR (δ)[a] | ¹³C NMR or ¹⁹F NMR (δ) | IR(thin film) cm⁻¹ |
|---|---|---|---|---|---|
| 5 | | 319 ([M + H]⁺) | (300 MHz, CDCl₃) δ 8.44 (d, J = 2.7 Hz, 1H), 7.78 (d, J = 8.7 Hz, 1H), 7.73-7.64 (m, 2H), 7.49 (dd, J = 8.6, 2.7 Hz, 1H), 7.16-7.07 (m, 2H), 4.39 (q, J = 7.1 Hz, 2H), 1.35 (t, J = 7.2 Hz, 3H) | | 2229, 1767 |
| 6 | | 300 ([M + H]⁺) | 8.37 (dd, J = 2.9, 0.6 Hz, 1H), 7.72 (dd, J = 8.8, 0.7 Hz, 1H), 7.39 (dd, J = 8.7, 2.9 Hz, 1H), 4.46 (q, J = 7.9 Hz, 2H), 4.37 (q, J = 7.1 Hz, 2H), 1.33 (t, J = 7.1 Hz, 3H) | ¹⁹F NMR −73.82 (s, 3F), −104.24 (s, 2F) | |
| 7 | | 363 ([M + H]⁺) | 8.54 (d, J = 2.5 Hz, 1H), 8.48-8.37 (m, 1H), 8.06-7.93 (m, 1H), 7.82 (dd, J = 8.6, 0.6 Hz, 1H), 7.72 (dd, J = 8.6, 2.6 Hz, 1H), 7.16 (d, J = 8.7 Hz, 1H), 4.40 (q, J = 7.1 Hz, 2H), 1.36 (t, J = 7.1 Hz, 3H) | | |
| 8 | | 328 ([M]⁺) | 8.51 (dd, J = 2.7, 0.7 Hz, 1H), 8.10 (dd, J = 2.7, 0.7 Hz, 1H), 7.78 (dd, J = 8.7, 0.7 Hz, 1H), 7.67 (dd, J = 8.6, 2.6 Hz, 1H), 7.01 (dd, J = 8.7, 0.7 Hz, 1H), 4.39 (q, J = 7.1 Hz, 2H), 1.35 (t, J = 7.1 Hz, 3H) | | |
| 9 | | 281 ([M + H]⁺) | ¹H NMR (400 MHz, CDCl₃) δ 8.71 (dd, J = 2.23, 0.57 Hz, 1H), 8.00 (dd, J = 8.4, 2.3 Hz, 1H), 7.65 (dd, J = 8.4, 0.7 Hz, 1H), 4.37 (q, J = 7.1 Hz, 2H), 1.33 (t, J = 7.1 Hz, 3H) | ¹⁹F NMR −105.2 (s) | |
| 10 | | | 8.59 (s, 1H), 7.85 (dd, J = 8.2, 1.4 Hz, 1H), 7.76 (d, J = 8.1 Hz, 1H), 4.38 (q, J = 7.1 Hz, 2H), 3.48 (q, J = 10.5 Hz, 2H), 1.33 (t, J = 7.1 Hz, 3H) | | 2990, 1768 |

[a] All ¹H NMR data measured in CDCl₃ at 400 MHz unless otherwise noted

Example 4: Preparation of 2-(5-(4-cyanophenoxy)pyridin-2-yl)-2,2-difluoro-N-methoxy-N-methylacetamide (11)

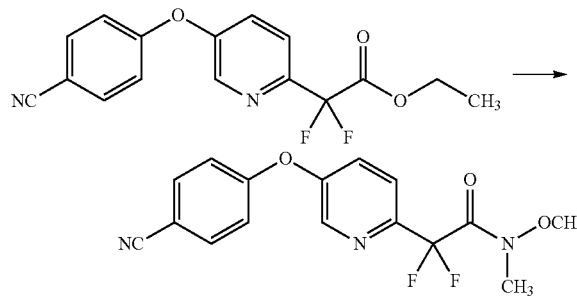

To a 1 L three neck round bottom flask equipped with an overhead stirrer, a temperature probe, a nitrogen inlet, and an addition funnel and cooled in an ice-water bath was charged N,O-dimethylhydroxylamine hydrochloride (6.15 g, 63 mmol) and dichloromethane (63 mL). A solution of dimethylaluminum chloride (63 mL, 63 mmol, 1M solution in hexane) was added slowly to keep the temperature below 15° C. Upon the completion of addition, the ice-water bath was removed and the reaction allowed to warm to room temperature for 1 h. A solution of ethyl 2-(5-(4-cyanophenoxy)pyridin-2-yl)-2,2-difluoroacetate (13.37 g, 42 mmol) in $CH_2Cl_2$ (21 mL) was added over 5-10 min and the mixture was stirred at rt for 3-5 h and the reaction proceeded to completion as indicated by HPLC. The reaction was cooled to 5° C. and quenched by a slow addition of 10% potassium sodium tartrate solution (400 mL). After addition of potassium sodium tartrate, the reaction mixture was stirred at room temperature for 1 h. After separation of the organic layer, the aqueous layer was extracted with additional $CH_2Cl_2$. The combined organic layers were washed with 10% $NaHCO_3$ and water. The organic layer was concentrated and replaced with heptane to solidify the product. The product was filtered, washed with heptane and dried overnight in vacuo to give the title compound as a light yellow solid (12 g, 86%).

The following compounds 11-18 in Table 4a were made in accordance with the reaction depicted in Scheme 4 and the procedures described in Example 4. Characterization data for compounds 11-18 are shown in Table 4b.

Scheme 4

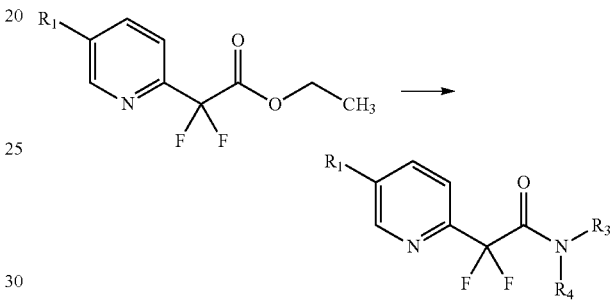

TABLE 4a

| Compound No. | $R_1$ | —N($R_3$)($R_4$) | Appearance | Prepared as in Example(s): |
|---|---|---|---|---|
| 11 | 4-NC-C6H4-O- | —N(OCH$_3$)(CH$_3$) | Light yellow solid | Ex 4 |
| 12 | 4-NC-C6H4-O- | —N(CH$_3$)(CH$_3$) | Oil | Ex 4 |
| 13 | 4-NC-C6H4-O- | —N(CH$_2$CH$_3$)(CH$_2$CH$_3$) | Oil | Ex 4 |
| 14 | 4-NC-C6H4-O- | morpholinyl | Clear oil | Ex 4 |
| 15 | F$_3$C-CH$_2$-O- | —N(OCH$_3$)(CH$_3$) | Off-white solid | Ex 4 |

TABLE 4a-continued

| Compound No. | R₁ | —N(R₃)(R₄) | Appearance | Prepared as in Example(s): |
|---|---|---|---|---|
| 16 | 5-(trifluoromethyl)pyridin-2-yloxy | —N(OCH₃)(CH₃) | Light yellow solid | Ex 4 |
| 17 | 5-chloropyridin-2-yloxy | —N(OCH₃)(CH₃) | Yellow solid | Ex 4 |
| 18 | 2,2,2-trifluoroethyl | —N(OCH₃)(CH₃) | Oil | Ex 4 |

TABLE 4b

| Compound No. | Mp (° C.) | ESIMS m/z | ¹H NMR (δ)ᵃ | ¹³C NMR or ¹⁹F NMR (δ) | IR(thin film) cm⁻¹ |
|---|---|---|---|---|---|
| 11 | 101 | 334 | 8.42 (d, J = 4.0 Hz, 1H), 7.71 (m, 3H), 7.49 (dd, J = 8.0, 4.0 Hz, 1H), 7.10 (m, 2H), 3.56 (s, 3H), 3.29 (s, 3H) | | |
| 12 | | 319 | 8.45 (dd, J = 2.8, 0.7 Hz, 1H), 7.81-7.63 (m, 3H), 7.50 (dd, J = 8.6, 2.8 Hz, 1H), 7.18-7.05 (m, 2H), 3.15 (t, J = 1.9 Hz, 3H), 3.07 (t, J = 0.8 Hz, 3H) | ¹⁹F NMR (376 MHz, CDCl₃) δ −97.58 (s) | |
| 13 | | 346 | 8.45 (d, J = 4.0 Hz, 1H), 7.72 (m, 3H), 7.49 (dd, J = 12.0, 4.0 Hz, 1H), 7.10 (m, 2H), 3.47 (m, 4H), 1.20 (m, 6H) | 162.28, 159.65, 153.10, 148.85, 141.36, 134.53, 127.39, 122.22, 118.95, 118.23, 114.24, 107.89, 42.24, 41.73, 14.16, 12.27 | |
| 14 | | 359 | (300 MHz, CDCl₃) δ 8.44 (d, J = 2.7 Hz, 1H), 7.76 (d, J = 8.6 Hz, 1H), 7.69 (m, 2H), 7.49 (dd, J = 8.7, 2.7 Hz, 1H), 7.11 (m, 2H), 3.70 (m, 8H) | | |
| 15 | | 315 ([M + H]⁺) | 8.34 (d, J = 2.9 Hz, 1H), 7.68 (d, J = 8.8 Hz, 1H), 7.41 (dd, J = 8.7, 2.9 Hz, 1H), 4.46 (q, J = 7.9 Hz, 2H), 3.49 (s, 3H), 3.27 (s, 3H) | ¹⁹F NMR −73.79 (s, 3F), −100.76 (s, 2F) | |
| 16 | | 378 ([M + H]⁺) | 8.52 (d, J = 2.4 Hz, 1H), 8.46-8.38 (m, 1H), 8.03-7.94 (m, 1H), 7.78 (dd, J = 8.6, 0.4 Hz, 1H), 7.72 (dd, J = 8.6, 2.5 Hz, 1H), 7.15 (d, J = 8.6 Hz, 1H), 3.50 (s, 3H), 3.29 (s, 3H) | | |
| 17 | | 343 ([M]⁺) | 8.49 (dd, J = 2.6, 0.8 Hz, 1H), 8.10 (dd, J = 2.6, 0.7 Hz, 1H), 7.78-7.70 (m, 2H), 7.67 (dd, J = 8.6, 2.6 Hz, 1H), 7.00 (dd, J = 8.7, 0.7 Hz, 1H), 3.50 (s, 3H), 3.29 (s, 3H) | | |

TABLE 4b-continued

| Compound No. | Mp (° C.) | ESIMS m/z | $^1$H NMR (δ)$^a$ | $^{13}$C NMR or $^{19}$F NMR (δ) | IR(thin film) cm$^{-1}$ |
|---|---|---|---|---|---|
| 18 | | 299 ([M + H]$^+$) | 8.56 (s, 1H), 7.83 (dd, J = 8.1, 1.6 Hz, 1H), 7.71 (d, J = 7.9 Hz, 1H), 3.46 (m, 5H), 3.28 (s, 3H) | | |

$^a$All $^1$H NMR data measured in CDCl$_3$ at 400 MHz unless otherwise noted

Example 5: Preparation of 4-((6-(2-(2,4-difluorophenyl)-1,1-difluoro-2-oxoethyl)pyridin-3-yl)oxy)benzonitrile (19)

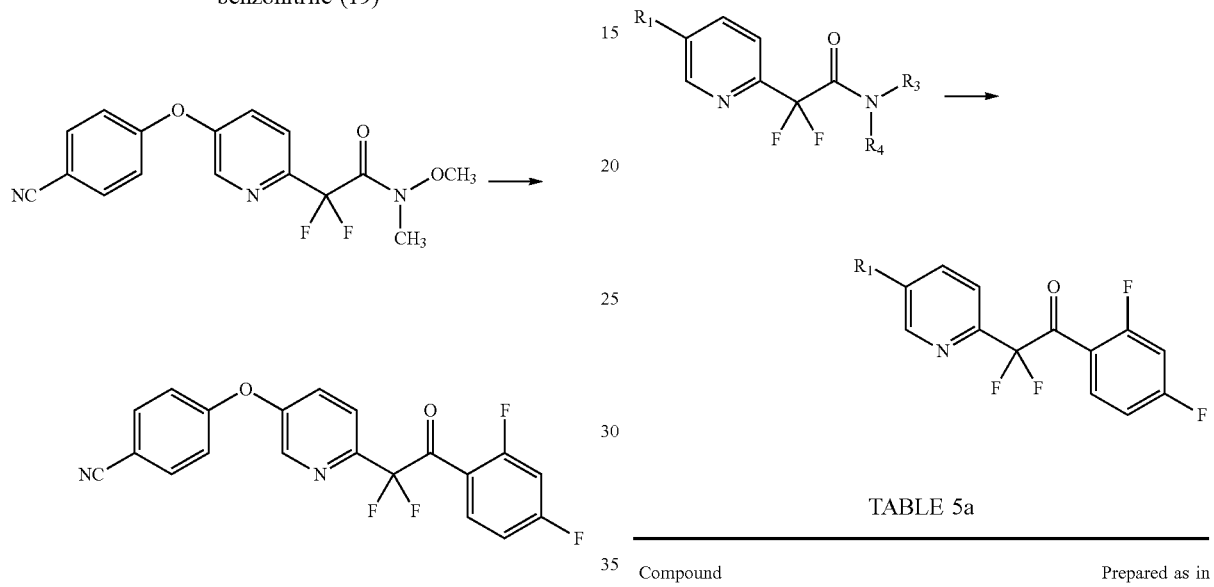

Scheme 5

To a magnetically stirred mixture of magnesium (2.43 g, 100 mmol) in THF (50 mL) under N$_2$ atmosphere was added a part of solution of 1-bromo-2,4-difluorobenzene (19.30 g, 11.3 mL, 100 mmol) in THF (25 mL) at 45° C. The solution was stirred for 0.5 h at 50-55° C. and cooled to 30° C. The rest of solution was charged slowly over 1 h at 30-40° C., and then the mixture was stirred for additional 1-2 h at room temperature.

Into the solution of 2-(5-(4-cyanophenoxy)pyridin-2-yl)-2,2-difluoro-N-methoxy-N-methylacetamide (16.6 g, 50 mmol) in THF (75 mL) at 0° C. was added the above freshly prepared Grignard solution slowly, and then the mixture was stirred for 0.5 h. After completion of reaction by HPLC, the reaction mixture was cooled to 5° C. (ice-water bath), followed by addition of 6N HCl (10 mL) and 20% NH$_4$Cl (200 mL). The product was extracted with CH$_2$Cl$_2$ (400 mL). The organic layer was washed with additional 20% NH$_4$Cl, 10% K$_2$CO$_3$ and water. The separated organic layer was concentrated and replaced with EtOH to give the title compound (19.3 g, 100%) that was used in the next step without further purification.

This reaction was also carried out as described in Example 5 with the exception of generating the arylmagnesium bromide reagent by reaction of the aryl bromide with isopropylmagnesium chloride.

The following compounds 19-23 in Table 5a were made in accordance with the reaction depicted in Scheme 5 and the procedures described in Example 5. Characterization data for compounds 19-23 are shown in Table 5b.

TABLE 5a

| Compound No. | R$_1$ | Appearance | Prepared as in Example(s): |
|---|---|---|---|
| 19 | NC-C$_6$H$_4$-O- | Yellow solid | Ex 5 |
| 20 | F$_3$C-CH$_2$-O- | Amber solid | Ex 5 |
| 21 | 5-(F$_3$C)pyridin-2-yl-O- | Brown oil | Ex 5 |
| 22 | 5-Cl-pyridin-2-yl-O- | Brown Oil | Ex 5 |
| 23 | F$_3$C-CH$_2$- | Yellow oil | Ex 5 |

TABLE 5b

| Compound No. | Mp (° C.) | ESIMS m/z | $^1$H NMR (δ)[a] | $^{13}$C NMR or $^{19}$F NMR (δ) | IR(thin film) cm$^{-1}$ |
|---|---|---|---|---|---|
| 19 | | 387 ([M + H]$^+$) | (300 MHz, CDCl$_3$) δ 8.36 (d, J = 2.7 Hz, 1H), 8.15-8.02 (m, 1H), 7.86 (d, J = 8.7 Hz, 1H), 7.74-7.65 (m, 2H), 7.53 (dd, J = 8.6, 2.7 Hz, 1H), 7.16-7.06 (m, 2H), 7.05-6.96 (m, 1H), 6.84 (ddd, J = 10.9, 8.6, 2.4 Hz, 1H) | $^{19}$F NMR (376 MHz, CDCl$_3$) δ −99.13 (d, J = 13.5 Hz), −100.67 (d, J = 14.9 Hz), −101.82 (dd, J = 28.5, 14.2 Hz) | |
| 20 | | 368 ([M + H]$^+$) | 8.29 (d, J = 2.8 Hz, 1H), 8.04 (td, J = 8.4, 6.4 Hz, 1H), 7.81 (d, J = 8.6 Hz, 1H), 7.44 (dd, J = 8.7, 2.9 Hz, 1H), 6.99 (dddd, J = 8.7, 7.6, 2.4, 0.9 Hz, 1H), 6.82 (ddd, J = 11.0, 8.6, 2.4 Hz, 1H), 4.45 (q, J = 7.8 Hz, 2H) | | |
| 21 | | 431 ([M + H]$^+$) | 8.53-8.37 (m, 1H), 8.09 (td, J = 8.4, 6.6 Hz, 1H), 8.05-7.97 (m, 1H), 7.90 (d, J = 8.5 Hz, 1H), 7.76 (dd, J = 8.6, 2.6 Hz, 1H), 7.15 (d, J = 8.6 Hz, 1H), 7.05-6.90 (m, 1H), 6.84 (ddd, J = 11.0, 8.7, 2.4 Hz, 1H) | | |
| 22 | | 396 ([M]$^+$) | 8.44 (dd, J = 2.6, 0.7 Hz, 1H), 8.12-8.03 (m, 2H), 7.86 (dd, J = 8.6, 0.7 Hz, 1H), 7.72 (ddd, J = 8.7, 4.4, 2.6 Hz, 2H), 7.04-6.96 (m, 2H), 6.84 (ddd, J = 11.0, 8.7, 2.4 Hz, 1H) | | |
| 23 | | 352 ([M + H]$^+$) | 8.51 (s, 1H), 8.08 (m, 1H), 7.88 (dd, J = 8.2, 1.7 Hz, 1H), 7.84 (dd, J = 8.1, 0.9 Hz, 1H), 7.00 (m, 1H), 6.83 (ddd, J = 10.8, 8.6, 2.4 Hz, 1H), 3.46 (q, J = 10.4 Hz, 2H) | | |

[a] All $^1$H NMR data measured in CDCl$_3$ at 400 MHz unless otherwise noted

Example 6. Preparation of 4-((6-(2-(2,4-difluorophenyl)-1,1-difluoro-2-oxoethyl)pyridin-3-yl)oxy)benzonitrile (19)

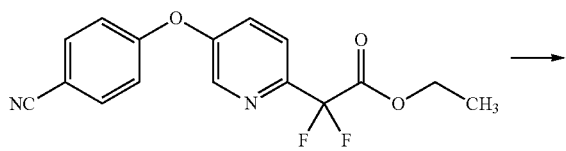

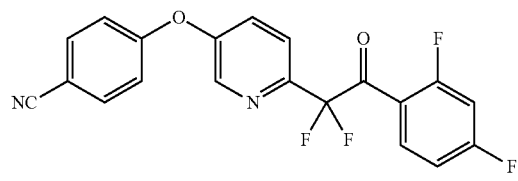

To a magnetically stirred mixture of 1-bromo-2,4-difluorobenzene (0.923 mL, 8.17 mmol) in Et$_2$O (21 mL) under N$_2$ atmosphere at −78° C. was added slowly n-butyllithium (2.5 M in hexanes, 3.27 mL, 8.17 mmol). After completion of the addition, ethyl 2-(5-(4-cyanophenoxy)pyridin-2-yl)-2,2-difluoroacetate (2.00 g, 6.28 mmol) in Et$_2$O (15 mL) was added, and the reaction was stirred at −60 to −50° C. for 1 h. The reaction was quenched with 2 N HCl until reaction mixture was acidic. The reaction was allowed to warm to room temperature, and the mixture then made basic with sat. aq. NaHCO$_3$ solution. The layers were separated, and the aqueous layer was extracted with Et$_2$O. The combined organic phases were dried (MgSO$_4$) and concentrated. The crude product was dried on the rotavap under vacuum for 4 h to give the title compound as a yellow oil (2.515 g, 88%).

Compounds 19 and 25 in Table 6a were made in accordance with the reaction depicted in Scheme 6 and the procedures described in Example 6. Characterization data for compound 25 is shown in Table 6b.

Scheme 6

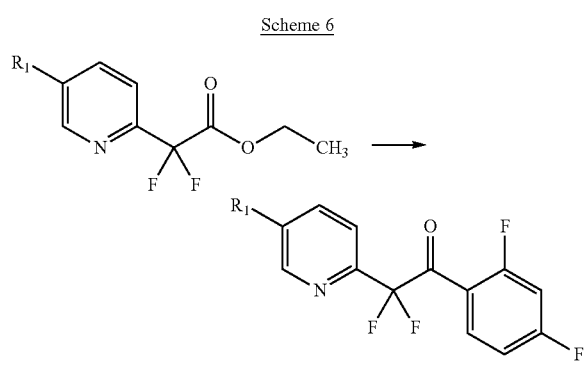

TABLE 6a

| Compound No. | $R_1$ | Appearance | Prepared as in Example(s): |
|---|---|---|---|
| 19 | (4-cyanophenoxy) | Yellow solid | Ex 6 |
| 25 | Br | White solid | Ex 6 |

TABLE 6b

| Compound No. | Mp (° C.) | ESIMS m/z | $^1$H NMR (δ)[a] | $^{13}$C NMR or $^{19}$F NMR (δ) | IR(thin film) cm$^{-1}$ |
|---|---|---|---|---|---|
| 25 | | 349 ([M + 1]$^+$) | 8.67-8.58 (m, 1H), 8.10-7.99 (m, 2H), 7.73 (dd, J = 8.4, 0.4 Hz, 1H), 7.05-6.94 (m, 1H), 6.83 (ddd, J = 10.7, 5.5, 1.4 Hz, 1H) | | |

[a] All $^1$H NMR data measured in CDCl$_3$ at 400 MHz unless otherwise noted

Example 7. Preparation of 4-((6-(2-(2,4-difluorophenyl)-1,1-difluoro-2-hydroxy-3-nitropropyl)pyridin-3-yl)oxy)benzonitrile (26)

Method A:
To a magnetically stirred solution of 4-((6-(2-(2,4-difluorophenyl)-1,1-difluoro-2-oxoethyl)pyridin-3-yl)oxy)benzonitrile (0.385 g, 0.897 mmol) in nitromethane (1.016 mL, 18.84 mmol) was added potassium carbonate (0.285 g, 2.063 mmol) under $N_2$ atmosphere. The reaction mixture was stirred at 40° C. for 2 h. The reaction was quenched with acetic acid (2.0 mL) in water (15 mL). The mixture was extracted with $Et_2O$, and the combined organic phases were washed with brine, sat. aq. $NaHCO_3$, and water, dried ($MgSO_4$) and concentrated to give the title compound as a yellow oil (427 mg, 99%).

Method B:
Into the mixture of 4-((6-(2-(2,4-difluorophenyl)-1,1-difluoro-2-oxoethyl)pyridin-3-yl)oxy)benzonitrile (50 mmol) and $K_2CO_3$ (6.9 g, 50 mmol) in EtOH (150 mL, 190 proof) at rt was charged nitromethane (9.16 g, 150 mmol) and the suspension was stirred at rt. Into the reaction mixture cooled to -10° C. was added 20% $NH_4Cl$ (150 mL). The mixture was stirred until a solid formed, followed by adding additional 20% $NH_4Cl$ (300 mL). The suspension was stirred for 1-2 h at room temperature. The product was isolated through filtration and washed with water and dried in vacuo to give the title compound (19.3 g, 86%).

This reaction was also carried out as described in Example 7, Method A with the exception of potassium hydroxide being used in place of potassium carbonate and dimethylformamide being used as a solvent instead of neat nitromethane.

The following compounds 26-31 in Table 7a were made in accordance with the reaction depicted in Scheme 7 and the procedures described in Example 7. Characterization data for compounds 26-31 are shown in Table 7b.

Scheme 7

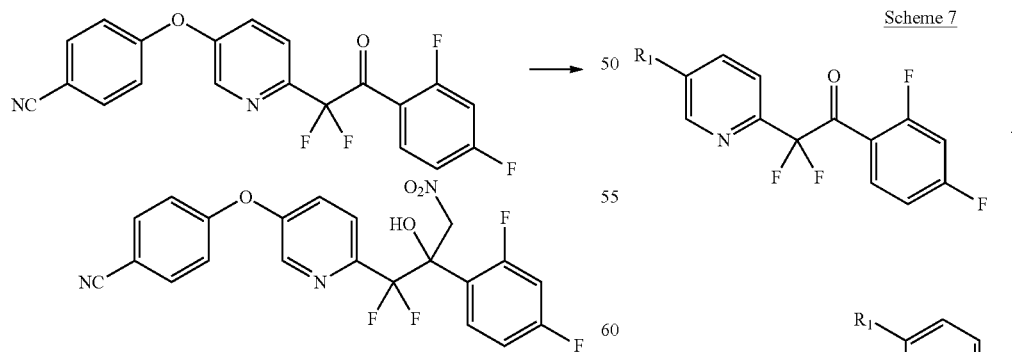

TABLE 7a

| Compound No. | R₁ | Appearance | Prepared as in Example(s): |
|---|---|---|---|
| 26 | 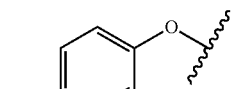 | White solid | Ex 7, Methods A and B |
| 27 | 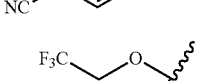 | Tan solid | Ex 7, Method B |
| 28 | 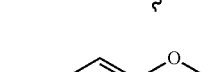 | Vanilla color solid | Ex 7, Method B |
| 29 |  | Black oil | Ex 7, Method B |
| 30 | Br | White solid | Ex 7, Method A |
| 31 |  | Solid | Ex 7, Method B |

TABLE 7b

| Compound No. | Mp (° C.) | ESIMS m/z | ¹H NMR (δ)ᵃ | ¹³C NMR or ¹⁹F NMR (δ) | IR(thin film) cm⁻¹ |
|---|---|---|---|---|---|
| 26 | | 448 ([M + H]⁺) | (300 MHz, CDCl₃) δ 8.40 (d, J = 2.7 Hz, 1H), 7.71 (m, 2H), 7.54 (m, 2H), 7.41 (dd, J = 8.7, 2.7 Hz, 1H), 7.10 (m, 2H), 6.83 (m, 2H), 6.16 (s, 1H), 5.63 (d, J = 12.7 Hz, 1H), 5.10 (dd, J = 12.7, 1.7 Hz, 1H) | | 3337, 2229 |
| 27 | | 429 ([M + H]⁺) | 8.35 (d, J = 2.9 Hz, 1H), 7.57-7.45 (m, 2H), 7.32 (dd, J = 8.8, 2.9 Hz, 1H), 6.87-6.75 (m, 2H), 6.36 (s, 1H), 5.62 (d, J = 12.6 Hz, 1H), 5.06 (dd, J = 12.6, 1.6 Hz, 1H), 4.45 (q, J = 7.8 Hz, 2H) | ¹⁹F NMR (376 MHz, CDCl₃) δ −78.68 (br), −104.97 (dd, J = 255.68, 15.04 Hz), −105.54 (m), −108.44 (d, J = 7.52 Hz), −109.49 (dd, J = 255.68, 15.04 Hz) | |
| 28 | | 492 ([M + 1]⁺) | 8.53 (d, J = 2.5 Hz, 1H), 8.41 (dd, J = 1.5, 0.8 Hz, 1H), 8.00 (dd, J = 8.6, 2.4 Hz, 1H), 7.68 (dd, J = 8.6, 2.6 Hz, 1H), 7.63-7.51 (m, 2H), 7.16 (d, J = 8.7 Hz, 1H), 6.94-6.79 (m, 2H), 6.48 (s, 1H), 5.66 (d, J = 12.6 Hz, 1H), 5.09 (dd, J = 12.6, 1.1 Hz, 1H) | ¹⁹F NMR (376 MHz, CDCl₃) δ −104.97 (d, J = 19.7 Hz), −105.43−−105.73 (m), −108.53 (d, J = 9.0 Hz), −108.76−−109.77 (m), 61.82 (s) | |
| 29 | | 457 ([M]⁺) | 8.50 (d, J = 2.6 Hz, 1H), 8.15-8.06 (m, 1H), 7.75 (dd, J = 8.7, 2.6 Hz, 1H), 7.64 (dd, J = 8.6, 2.6 Hz, 1H), 7.57 (dd, J = 8.7, 0.8 Hz, 2H), 7.02 (dd, J = 8.7, 0.6 Hz, 1H), 6.89-6.78 (m, 2H), 6.57 (s, 1H), 5.64 (d, J = 12.5 Hz, 1H), 5.14-5.00 (m, 1H) | | |
| 30 | | 409 ([M]⁺) | 8.68 (d, J = 2.2 Hz, 1H), 7.94 (dd, J = 8.4, 2.2 Hz, 1H), 7.53-7.45 (m, 1H), 7.41 (d, J = 8.4 Hz, 1H), 6.87-6.77 (m, 2H), 5.93 (s, 1H), 5.65 (d, J = 12.8 Hz, 1H), 5.08 (dd, J = 12.8, 1.7 Hz, | ¹⁹F NMR (376 MHz, CDCl₃) δ −105.51 (ddd, J = 30.0, 17.6, 9.5 Hz), −106.02 (dd, J = 258.3, 17.4 Hz), −108.03 (d, J = 9.5 Hz), −110.56 | |

TABLE 7b-continued

| Compound No. | Mp (° C.) | ESIMS m/z | $^1$H NMR (δ)[a] | $^{13}$C NMR or $^{19}$F NMR (δ) | IR(thin film) cm$^{-1}$ |
|---|---|---|---|---|---|
| | | | 1H) | (dd, J = 258.2, 30.5 Hz) | |
| 31 | | 413 ([M + H]$^+$) | 8.56 (s, 1H), 7.78 (dd, J = 8.1, 1.6 Hz, 1H), 7.51 (m, 2H), 6.81 (m, 2H), 6.40 (s, 1H), 5.64 (d, J = 12.6 Hz, 1H), 5.08 (dd, J = 12.6, 1.4 Hz, 1H), 3.46 (q, J = 10.3 Hz, 2H) | | |

[a]All $^1$H NMR data measured in CDCl$_3$ at 400 MHz unless otherwise noted

Example 8. Preparation of 4-((6-(3-amino-2-(2,4-difluorophenyl)-1,1-difluoro-2-hydroxypropyl)pyridin-3-yl)oxy)benzonitrile (32)

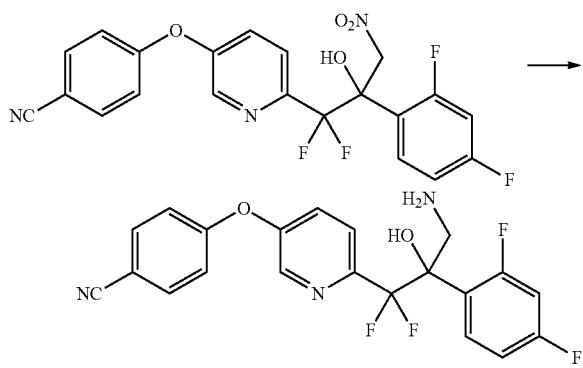

Method A. By Reduction with Zinc Powder:

To a solution of 4-((6-(2-(2,4-difluorophenyl)-1,1-difluoro-2-hydroxy-3-nitropropyl)pyridin-3-yl)oxy)benzonitrile (0.412 g, 0.921 mmol) in acetic acid (3.68 mL) was added zinc powder (0.602 g, 9.21 mmol). The reaction was stirred at rt. After 1 h, LCMS indicated a complete conversion to the desired product. The reaction was filtered through a plug of celite and washed with acetic acid. The filtrate was concentrated to 1 mL by co-evaporating with acetonitrile and was neutralized with sat. aq. NaHCO$_3$. The mixture was extracted with EtOAc. The combined organic phases were dried (MgSO$_4$) and concentrated to give the acetic acid salt of the desired product. The residue was diluted with CH$_2$Cl$_2$, and the organic phase was washed with saturated aqueous NaHCO$_3$, brine, and then dried (MgSO$_4$) and concentrated to give the title compound as a faint yellow foam (296 mg, 77%).

Method B. By Reduction with Tin(II) Chloride:

To a magnetically stirred solution of 4-((6-(2-(2,4-difluorophenyl)-1,1-difluoro-2-hydroxy-3-nitropropyl)pyridin-3-yl)oxy)benzonitrile (0.208 g, 0.465 mmol) (contaminated by 29 mg of nitromethane=0.47 mmol) in ethanol (4.65 mL) was added a solution of anhydrous tin(II) chloride (0.529 g, 2.79 mmol) in HCl (0.848 mL, 27.9 mmol). The reaction mixture was stirred at 60° C. for 4 h. The reaction mixture was poured into ice water and was neutralized with sat. aq. NaHCO$_3$. The mixture was filtered through celite while washing with EtOAc. The filtrate was extracted with EtOAc, and the combined organic phases were washed with brine and water, dried (MgSO$_4$) and concentrated. Purification by silica gel chromatography (0-15% MeOH/DCM) gave the title compound as a faint yellow oil (62 mg, 31.9%).

Method C. By Reduction with Zinc Powder:

Into the flask (500 mL) containing Zn (13.08 g, 200 mmol) in AcOH (40 mL) at 23° C. was added slowly a solution of 4-((6-(2-(2,4-difluorophenyl)-1,1-difluoro-2-hydroxy-3-nitropropyl)pyridin-3-yl)oxy)benzonitrile (8.95 g, 20 mmol) in MeOH (160 mL) at 30-35° C. over 20 min. The mixture was stirred at rt. After completion of reaction, the reaction mixture was diluted with CH$_2$Cl$_2$ (200 mL) and filtered through celite which was rinsed with additional CH$_2$Cl$_2$. The resulting solution was washed with 10% NH$_4$Cl solution. After separation, the aq. layer was extracted with additional CH$_2$Cl$_2$. The combined organic layers were washed with 10% KOH (100 mL) and water (50 mL). The organic layer was concentrated with acetonitrile, and the crude title compound was used in the next step without further purification.

The following compounds 32-37 in Table 8a were made in accordance with the reaction depicted in Scheme 8 and the procedures described in Example 8. Characterization data for compounds 32-37 are shown in Table 8b.

Scheme 8

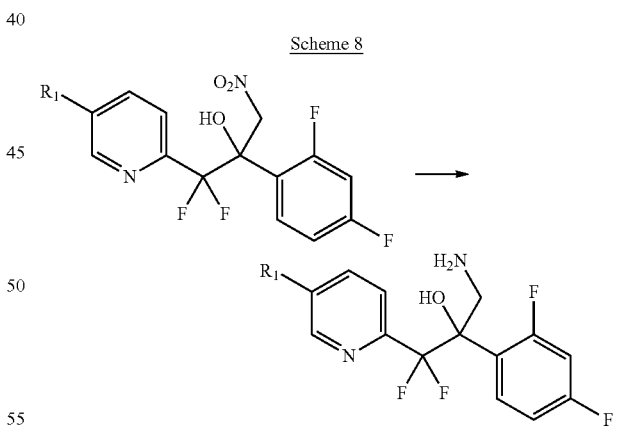

TABLE 8a

| Compound No. | R$_1$ | Appearance | Prepared as in Example(s): |
|---|---|---|---|
| 32 | | Faint yellow foam | Ex 8, Methods A, B and C |

TABLE 8a-continued

| Compound No. | R₁ | Appearance | Prepared as in Example(s): |
|---|---|---|---|
| 33 | F₃C-O- (trifluoroethoxy) | Oil | Ex 8, Method C |
| 34 | 5-(trifluoromethyl)pyridin-2-yloxy | Light brown oil | Ex 8, Method C |
| 35 | 5-chloropyridin-2-yloxy | Light Yellow solid | Ex 8, Method C |
| 36 | Br | Colorless oil | Ex 8, Method A |
| 37 | F₃C-CH₂- (3,3,3-trifluoropropyl) | Nearly white solid | Ex 8, Method C |

TABLE 8b

| Compound No. | Mp (° C.) | ESIMS m/z | ¹H NMR (δ)ᵃ | ¹³C NMR or ¹⁹F NMR (δ) | IR(thin film) cm⁻¹ |
|---|---|---|---|---|---|
| 32 | | 418 ([M + H]⁺) | (300 MHz, CDCl₃) δ 8.36 (d, J = 2.6 Hz, 1H), 7.67 (m, 2H), 7.50 (m, 1H), 7.44 (app d, J = 8.6 Hz, 1H), 7.36 (dd, J = 8.6, 2.7 Hz, 1H), 7.05 (m, 2H), 6.76 (m, 2H), 3.84 (dd, J = 13.7, 4.2 Hz, 1H), 3.21 (d, J = 13.5 Hz, 1H), 2.47 (br s, 2H) | | 3419, 3076, 2228 |
| 33 | | | 8.31 (d, J = 2.9 Hz, 1H), 7.50 (td, J = 8.7, 6.6 Hz, 1H), 7.39 (d, J = 8.7 Hz, 1H), 7.29-7.21 (m, 1H), 6.76 (dddd, J = 14.3, 11.5, 8.5, 2.6 Hz, 2H), 6.29 (s, 1H), 4.43 (q, J = 7.9 Hz, 2H), 3.79 (dd, J = 13.6, 4.4 Hz, 1H), 3.22 (d, J = 13.8 Hz, 1H), 1.44-1.07 (m, 2H) | | |
| 34 | | 460 ([M − 1]⁻) | 8.48 (d, J = 2.5 Hz, 1H), 8.41 (dd, J = 1.6, 0.8 Hz, 1H), 8.02-7.92 (m, 1H), 7.62-7.47 (m, 3H), 7.13 (d, J = 8.6 Hz, 1H), 6.88-6.72 (m, 2H), 6.35-6.33 (m, 1H), 3.80 (dd, J = 13.7, 4.2 Hz, 1H), 3.26 (d, J = 13.7 Hz, 1H), 0.9-1.6 (br, 2H) | | |
| 35 | | 457 ([M]⁺) | 8.45 (d, J = 2.7 Hz, 1H), 8.09 (dd, J = 2.6, 0.7 Hz, 1H), 7.72 (dd, J = 8.7, 2.6 Hz, 1H), 7.62-7.53 (m, 2H), 7.49 (dd, J = 8.6, 0.7 Hz, 1H), 6.99 (dd, J = 8.7, 0.7 Hz, 1H), 6.79 (dddd, J = 20.5, 11.5, 8.7, 2.4 Hz, 2H), 5.30 (s, 2H), 3.83-3.63 (m, 1H), 3.28 (d, J = 12.6 Hz, 1H), 1.47 (s, 1H) | | |
| 36 | | 379 ([M]⁺) | 8.62 (dd, J = 7.0, 2.1 Hz, 1H), 7.85 (dd, J = 8.4, 2.3 Hz, 1H), 7.52-7.41 (m, 1H), 7.30 (dd, J = 8.4, 0.5 Hz, 1H), 6.84-6.68 (m, 2H), 3.87 (dd, J = 13.7, 4.7 Hz, 1H), 3.19 (d, J = 13.7 Hz, 1H), 1.0-1.9 (br, 2H), 0.8-0.9 (br, 1H) | ¹⁹F NMR (376 MHz, CDCl₃) δ −106.15 (ddd, J = 23.2, 15.0, 8.3 Hz), −109.39 (dd, J = 252.1, 23.3 Hz), −110.47 (d, J = 8.8 Hz), −110.99 (dd, J = 252.2, 14.9 Hz) | |
| 37 | | 383 ([M + H]⁺) | 8.53-8.49 (m, 1H), 7.69 (dd, J = 8.1, 2.1 Hz, 1H), 7.55-7.41 (m, 2H), 6.82-6.70 (m, 2H), 3.80 (dd, J = 13.6, 4.4 Hz, 1H), 3.43 (q, | ¹⁹F NMR −65.75 (s, 3F), ABX: X = −106.29 (ddd, J = 22.0, 15.9, 8.6 Hz, 1F), | |

TABLE 8b-continued

| Compound No. | Mp (° C.) | ESIMS m/z | $^1$H NMR (δ)$^a$ | $^{13}$C NMR or $^{19}$F NMR (δ) | IR(thin film) cm$^{-1}$ |
|---|---|---|---|---|---|
| | | | J = 10.5 Hz, 2H), 3.23 (dq, J = 13.8, 1.1 Hz, 1H) | B = −109.27 (JAB = 254.7 Hz, JBX = 21.9 Hz, 1F), −110.61 (d, J = 8.4 Hz, 1F), A = −111.04 (JAB = 254.7, JAX = 15.9 Hz, 1F) | |

$^a$All $^1$H NMR data measured in CDCl$_3$ at 400 MHz unless otherwise noted

Example 9. Preparation of 4-((6-(2-(2,4-difluorophenyl)-1,1-difluoro-2-hydroxy-3-(1H-tetrazol-1-yl)propyl)pyridin-3-yl)oxy)benzonitrile (38)

The following compounds 38-43 in Table 9a were made in accordance with the reaction depicted in Scheme 9 and the procedures described in Example 9. Characterization data for compounds 38-43 are shown in Table 9b.

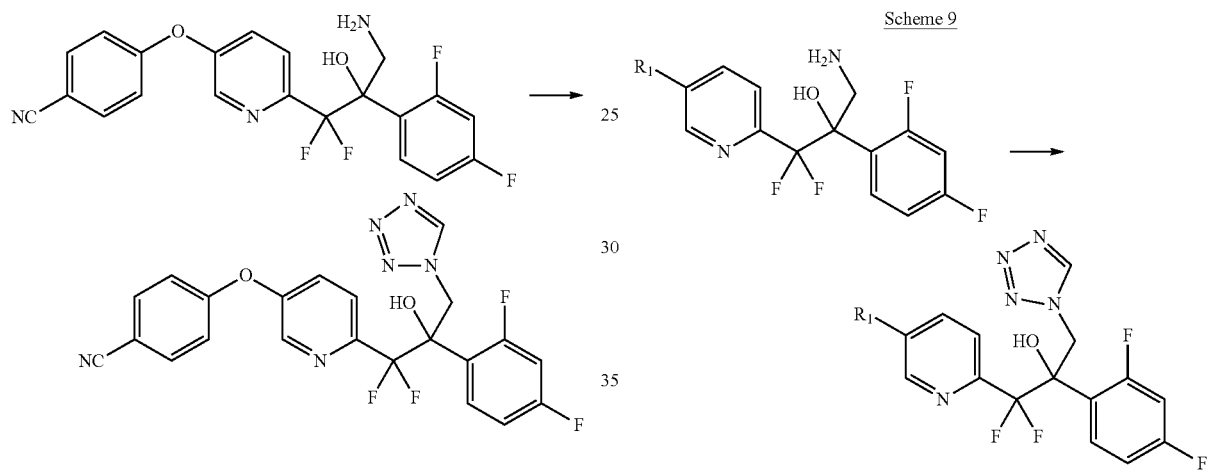

Scheme 9

Method A:

To a magnetically stirred solution of 4-((6-(3-amino-2-(2,4-difluorophenyl)-1,1-difluoro-2-hydroxypropyl)pyridin-3-yl)oxy)benzonitrile (0.060 g, 0.144 mmol) in acetic acid (0.288 mL) was added sodium azide (0.019 g, 0.288 mmol) and triethyl orthoformate (0.072 mL, 0.431 mmol). The reaction mixture was stirred at 90° C. for 5 h. The reaction mixture was poured into water and then made basic by addition of sat. aq. NaHCO$_3$ and the mixture extracted with CH$_2$Cl$_2$. The combined organic phases were dried (MgSO$_4$) and concentrated to give the title compound as a faint yellow oil (45 mg, 63.2%).

Method B:

To a magnetically stirred solution of 4-((6-(3-amino-2-(2,4-difluorophenyl)-1,1-difluoro-2-hydroxypropyl)pyridin-3-yl)oxy)benzonitrile (20 mmol) in acetonitrile was added AcOH (80 mL), sodium azide (2.6 g, 40 mmol) and triethyl orthoformate (8.89 g, 60 mmol) at room temperature. The reaction mixture was stirred at room temperature for 0.5 h and heated to 35-40° C. for 20 hours. After completion of reaction by HPLC, the reaction mixture was concentrated with additional acetonitrile and MeOH. The resulting residual oil was dissolved in MeOH (40 mL), and then the solution was charged slowly to water (300 mL) at room temperature. The precipitated solid was stirred for 2-3 h at room temperature. The suspension was filtered and washed with water. The cake was dried under vacuum at room temperature to give the title compound (9.02 g, 94%).

TABLE 9a

| Compound No. | R$_1$ | Appearance | Prepared as in Example(s): |
|---|---|---|---|
| 38 | 4-cyanophenoxy | off-white solid | Ex 9, Methods A and B |
| 39 | CF$_3$CH$_2$O— | Foam | Ex 9, Method B |
| 40 | 5-(trifluoromethyl)pyridin-2-yloxy | Pink colored foam | Ex 9, Method B |
| 41 | 5-chloropyridin-2-yloxy | Dark yellow solid | Ex 9, Method B |
| 42 | Br | Light brown thick oil | Ex 9, Method A |

TABLE 9a-continued

| Compound No. | R₁ | Appearance | Prepared as in Example(s): |
|---|---|---|---|
| 43 | F₃C-CH₂-* | Slightly yellowed glass | Ex 9, Method B |

TABLE 9b

| Compound No. | Mp (° C.) | ESIMS m/z | ¹H NMR (δ)ᵃ | ¹³C NMR or ¹⁹F NMR (δ) | IR(thin film) cm⁻¹ |
|---|---|---|---|---|---|
| 38 | | 469 ([M − H]⁻) | (300 MHz, CDCl₃) δ 8.74 (s, 1H), 8.26 (d, J = 2.7 Hz, 1H), 7.71 (m, 2H), 7.62 (d, J = 8.7 Hz, 1H), 7.43 (m, 2H), 7.19 (s, 1H), 7.12 (m, 2H), 6.76 (m, 2H), 5.44 (d, J = 14.4 Hz, 1H), 5.23 (dd, J = 14.4, 1.5 Hz, 1H) | ¹⁹F NMR (376 MHz, CDCl₃) δ −104.05 (m), −105.67 (dd, J = 263.9, 20.1 Hz), −107.32 (dd, J = 264.1, 34.3 Hz), −107.83 (d, J = 9.6 Hz) | |
| 39 | | 452 ([M + H]⁺) | 8.75 (s, 1H), 8.27 (d, J = 2.9 Hz, 1H), 7.57 (d, J = 8.8 Hz, 1H), 7.36-7.28 (m, 2H), 7.26 (s, 1H), 6.76 (ddd, J = 12.0, 8.5, 2.6 Hz, 1H), 6.71-6.62 (m, 1H), 5.57 (dd, J = 14.3, 0.8 Hz, 1H), 5.12 (dd, J = 14.3, 1.5 Hz, 1H), 4.44 (q, J = 7.8 Hz, 2H) | ¹⁹F NMR (376 MHz, CDCl₃) δ −73.68 (m), −103.79 (dd, J = 263.2, 41.46 Hz), −104.93 (m), 108.00 (d, J = 11.28 Hz), −110.45 (dd, J = 263.2, 41.46 Hz) | |
| 40 | | 515 ([M + H]⁺) | 8.79 (s, 1H), 8.48 (d, J = 2.4 Hz, 1H), 8.41 (dd, J = 1.6, 0.8 Hz, 1H), 8.01 (dd, J = 8.6, 2.4 Hz, 1H), 7.68 (dt, J = 18.4, 5.5 Hz, 2H), 7.37 (td, J = 8.9, 6.5 Hz, 2H), 7.17 (d, J = 8.6 Hz, 1H), 6.82-6.72 (m, 1H), 6.72-6.62 (m, 1H), 5.64 (d, J = 14.3 Hz, 1H), 5.13 (d, J = 14.4 Hz, 1H) | | |
| 41 | 61-63 | 480 ([M]⁺) | 8.76 (s, 1H), 8.53-8.39 (m, 1H), 8.09 (dd, J = 2.7, 0.7 Hz, 1H), 7.75 (dd, J = 8.7, 2.6 Hz, 1H), 7.71-7.53 (m, 2H), 7.35 (td, J = 8.9, 6.4 Hz, 1H), 7.02 (dd, J = 8.7, 0.7 Hz, 1H), 6.77 (ddd, J = 12.0, 8.5, 2.6 Hz, 1H), 6.72-6.66 (m, 1H), 5.68-5.58 (m, 1H), 5.14-5.07 (m, 1H), 2.10 (s, 1H) | | |
| 42 | | 432.11 ([M]⁺) | 8.76 (s, 1H), 8.63 (d, J = 1.4 Hz, 1H), 7.95 (dd, J = 8.4, 2.2 Hz, 1H), 7.46 (d, J = 8.4 Hz, 1H), 7.34-7.23 (m, 1H), 6.93 (s, 1H), 6.81-6.72 (m, 1H), 6.72-6.62 (m, 1H), 5.61 (d, J = 14.3 Hz, 1H), 5.12 (d, J = 14.8 Hz, 1H) | ¹⁹F NMR (376 MHz, CDCl₃) δ −103.52--103.97 (m), −103.96--104.40 (m), −107.62 (d, J = 9.7 Hz), −112.16 (dd, J = 263.2, 43.0 Hz) | |
| 43 | | 436 ([M + H]⁺) | 8.76 (s, 1H), 8.49 (d, J = 2.0 Hz, 1H), 7.79 (dd, J = 8.1, 2.1 Hz, 1H), 7.60 (d, J = 8.1 Hz, 1H), 7.37-7.28 (m, 2H), 6.76 (ddd, J = 12.1, 8.5, 2.6 Hz, 1H), 6.65 (dddd, J = 8.7, 7.5, 2.6, 0.9 Hz, 1H), 5.59 (dd, J = 14.3, | ¹⁹F NMR (376 MHz, CDCl₃) δ −65.61 (s, 3F), ABX: X= −103.93 (ddd, JAX = 41.9 Hz, JAB = 15.4, 9.8 Hz, 1F), B = −104.75 (JAB = 262.9 Hz, JBX = 15.5 Hz, 1F), −107.91 (d, J = | |

TABLE 9b-continued

| Compound No. | Mp (° C.) | ESIMS m/z | $^1$H NMR (δ)[a] | $^{13}$C NMR or $^{19}$F NMR (δ) | IR(thin film) cm$^{-1}$ |
|---|---|---|---|---|---|
| | | | 0.9 Hz, 1H), 5.13 (dd, J = 14.1, 1.4 Hz, 1H), 3.45 (q, J = 10.3 Hz, 2H) | 9.7 Hz, 1F), A = −111.65 (JAB = 262.9 Hz, JAX = 41.6 Hz, 1F) | |

[a]All $^1$H NMR data measured in CDCl$_3$ at 400 MHz unless otherwise noted

What is claimed is:

1. A method of making compounds of Formula III, including the step of:

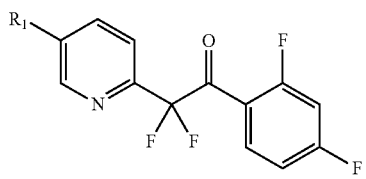
(III)

contacting compounds of Formula IIa with a preformed organometallic reagent,

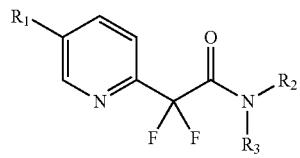
(IIa)

wherein
R$_1$ is

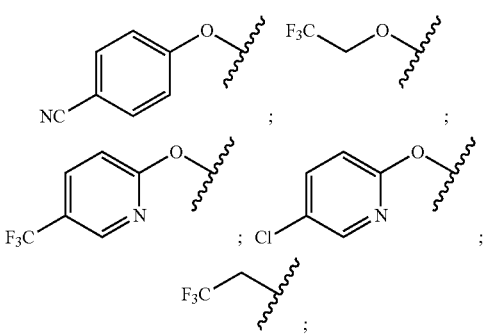

or
Br; and
R$_2$ and R$_3$ are selected from —OCH$_3$, —CH$_3$, —CH$_2$CH$_3$ or joined together to form a morpholine ring.

2. The method of claim 1, wherein the preformed organometallic reagent is formed by a metal halogen exchange reaction of 1-bromo-2,4-difluorobenzene with one of magnesium, n-butyllithium, and isopropylmagnesium chloride.

3. The method of claim 1, wherein the step of contacting compounds of Formula IIa with the preformed organometallic reagent further includes an aprotic solvent.

4. The method of claim 3, wherein the aprotic solvent is one of diethyl ether and tetrahydrofuran.

5. The method of claim 1 wherein the step of contacting compounds of Formula IIa with the preformed organometallic reagent is carried out at about 0° C.

6. The method of claim 1, further comprising the step of: contacting compounds of Formula II with an amine, a Lewis acid, and a solvent

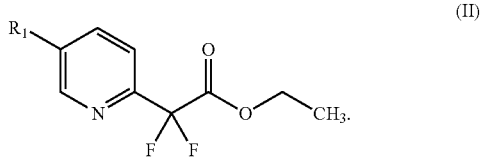
(II)

7. The method of claim 6, wherein the amine is selected from N,O-dimethylhydroxylamine, dimethylamine, diethylamine and morpholine.

8. The method of claim 6, wherein the Lewis acid is dimethylaluminum chloride.

9. The method of claim 6, wherein the solvent is dichloromethane.

10. The method of claim 6, wherein the step of contacting compounds of Formula II with the amine, the Lewis acid, and the solvent is carried out in such a manner as to maintain a temperature below about 15° C.

11. The method of claim 6, further comprising the step of: contacting compounds of the Formula I with ethyl 2-bromo-2,2-difluoroacetate and a metal

(I)

12. The method of claim 11, wherein the metal is copper.

13. The method of claim 11, wherein the step of contacting I with ethyl 2-bromo-2,2-difluoroacetate and a metal further includes a solvent.

14. The method of claim 13, wherein the solvent is selected from dimethyl sulfoxide, dimethylformamide, and mixtures thereof.

15. The method of claim 11, further comprising the step of:
Contacting 6-bromopyridin-3-ol with one of 5-chloro-2-fluoropyridine and 2-fluoro-5-(trifluoromethyl)pyridine.

16. The method of claim 15, wherein the step of contacting 6-bromopyridin-3-ol with one of 5-chloro-2-fluoropyridine and 2-fluoro-5-(trifluoromethyl)pyridine further includes a base.

17. The method of claim 16, wherein the base is one of cesium carbonate and potassium carbonate.

18. The method of claim 15, wherein the step of contacting 6-bromopyridin-3-ol with one of 5-chloro-2-fluoropyridine and 2-fluoro-5-(trifluoromethyl)pyridine further includes a solvent.

19. The method of claim 18, wherein the solvent is one of dimethyl sulfoxide and dimethylformamide.

20. The method of claim 15 wherein the step of contacting 6-bromopyridin-3-ol with one of 5-chloro-2-fluoropyridine and 2-fluoro-5-(trifluoromethyl)pyridine is carried out between 65° C. and 100° C.

21. The method of claim 11, further comprising the step of:

Contacting 6-bromopyridin-3-ol with 2,2,2-trifluoroethyl trifluoromethanesulfonate.

\* \* \* \* \*